United States Patent [19]

Weller, III et al.

[11] Patent Number: 4,638,010

[45] Date of Patent: Jan. 20, 1987

[54] ESTER SUBSTITUTED AMINOALKANOYLUREIDO AMINO AND IMINO ACID AND ESTER COMPOUNDS

[75] Inventors: Harold N. Weller, III; Eric M. Gordon, both of Pennington, N.J.

[73] Assignee: E. R. Squibb & Sons, Inc., Princeton, N.J.

[21] Appl. No.: 707,123

[22] Filed: Feb. 28, 1985

[51] Int. Cl.$^4$ .................. C07D 207/04; A61K 31/40; A61K 31/34; A61K 31/38

[52] U.S. Cl. ............................. 514/423; 544/282; 514/333; 514/339; 514/341; 514/343; 514/397; 514/414; 546/14; 546/147; 546/256; 546/268; 546/273; 546/276; 546/278; 546/281; 548/188; 548/336; 548/356; 548/406; 548/409; 548/454; 548/452; 548/455; 548/456; 548/465; 548/467; 548/468; 548/517; 548/527; 548/533; 548/953; 560/16

[58] Field of Search ............... 514/423, 333, 339, 341, 514/343, 397, 414; 548/533, 336, 467, 468, 517, 527; 546/256, 273, 276, 278, 281

[56] References Cited

U.S. PATENT DOCUMENTS 4,329,473  5/1982  Almquist et al. .............. 546/281
4,402,969  9/1983  Greenlee et al. .............. 514/423
4,470,793  9/1984  Natarajan et al. ............. 546/245 X

FOREIGN PATENT DOCUMENTS 17203  1/1984  Australia .
58-170752  10/1983  Japan ........................... 548/533
59-33260  2/1984  Japan .

OTHER PUBLICATIONS

Meyer et al., "Novel Synthesis of . . . ", J. Med. Chem., 1981, vol. 24, pp. 964–969.
Almquist et al., "Derivatives of Potent Angiotensin Converting Enzyme Inhibitor . . . ", J. Med. Chem., 1982, vol. 25, 1292–1299.

Primary Examiner—Joseph Paul Brust
Attorney, Agent, or Firm—Lawrence S. Levinson; Stephen B. Davis

[57] ABSTRACT

Compounds of the formula

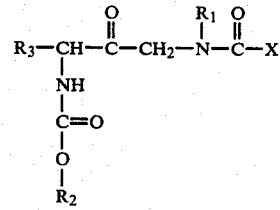

are disclosed. These compounds are useful as hypotensive agents due to their angiotensin converting enzyme inhibition activity and depending upon the definition of X may also be useful as analgesics due to their enkephalinase inhibition activity.

13 Claims, No Drawings

ESTER SUBSTITUTED AMINOALKANOYLUREIDO AMINO AND IMINO ACID AND ESTER COMPOUNDS

BACKGROUND OF THE INVENTION

Natarajan et al. in Australian Patent Application No. 17,203 disclose acylalkylaminocarbonyl substituted amino and imino acid compounds of the formula

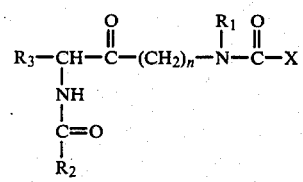

wherein $R_2$ is certain aryl, aralkyl, hetero, or alkylene-hetero groups. These compounds possess angiotensin converting enzyme inhibition activity and enkephalinase inhibition activity depending upon the definition of X.

Almquist et al. in U.S. Pat. No. 4,329,473 disclose angiotensin converting enzyme inhibiting compounds of the formula

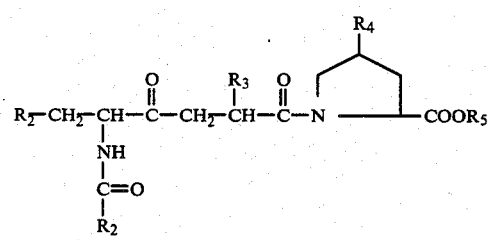

wherein $R_2$ is aryl, alkyl, alkoxy or benzyloxy.

SUMMARY OF THE INVENTION

This invention is directed to novel compounds of the formula

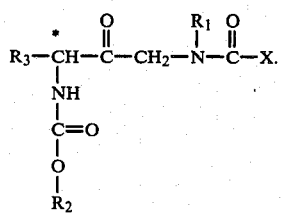

(I)

X is an amino or imino acid or ester of the formula

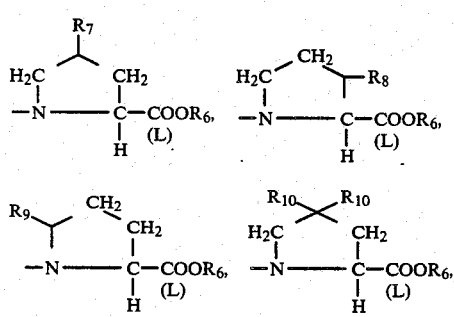

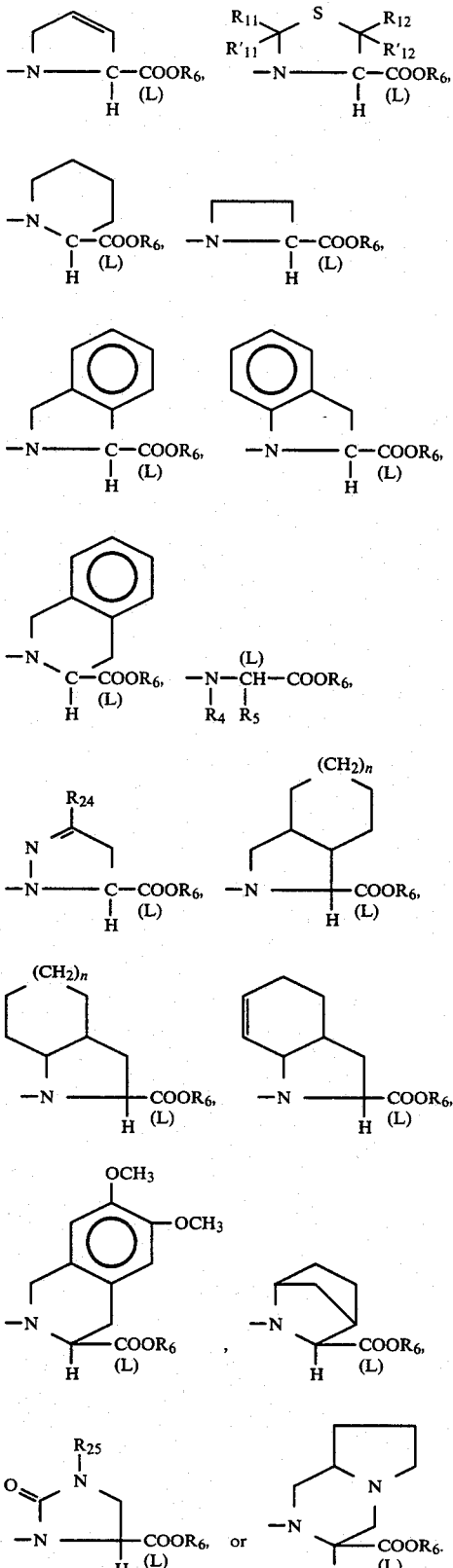

$n$ is zero, one or two.

$R_{25}$ is lower alkyl of 1 to 4 carbons or

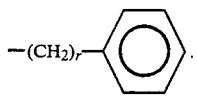
$R_7$ is hydrogen, lower alkyl, halogen, hydroxy,
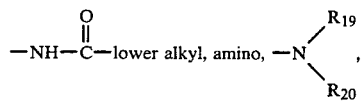
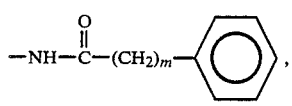
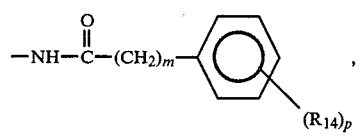
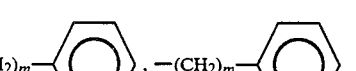
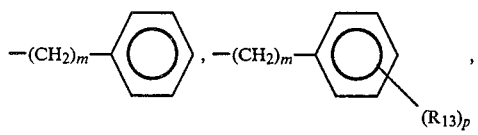
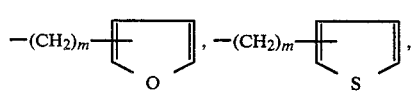
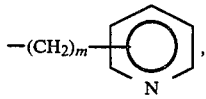
a 1- or 2-naphthyl of the formula
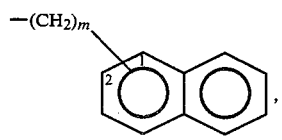
a substituted 1- or 2-naphthyl of the formula
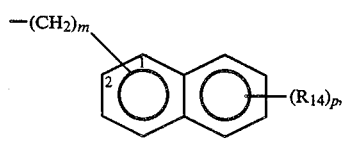
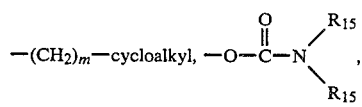
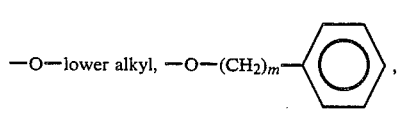
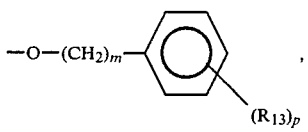
a 1- or 2-naphthyloxy of the formula
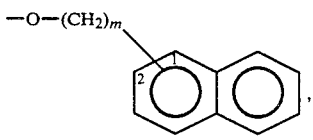
a substituted 1- or 2-naphthyloxy of the formula
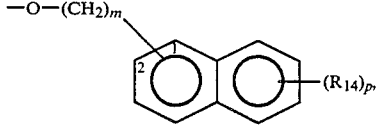
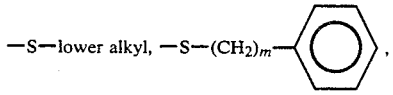
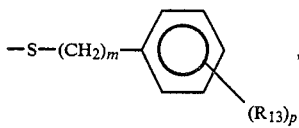
a 1- or 2-naphthylthio of the formula
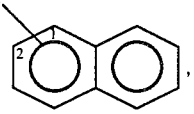
or a substituted 1- or 2-naphthylthio of the formula
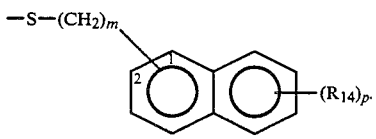
$R_8$ is halogen,
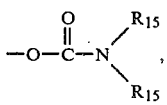
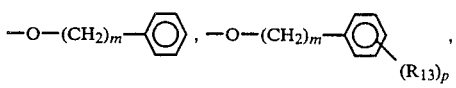
—O—lower alkyl, a 1- or 2-naphthyloxy of the formula

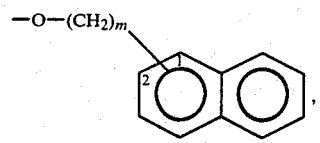

a substituted 1- or 2-naphthyloxy of the formula

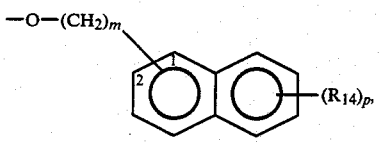

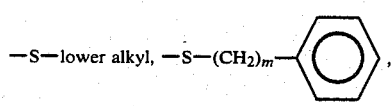

a 1- or 2-naphthylthio of the formula

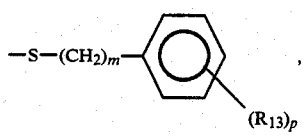

or a substituted 1- or 2-naphthylthio of the formula

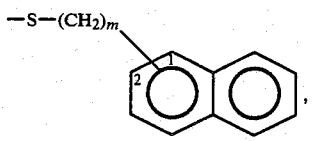

$R_9$ is keto,

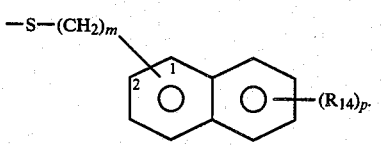

$R_{10}$ is halogen or $-Y-R_{16}$.

$R_{11}$, $R'_{11}$, $R_{12}$ and $R'_{12}$ are independently selected from hydrogen and lower alkyl or $R'_{11}$, $R_{12}$ and $R'_{12}$ are hydrogen and $R_{11}$ is

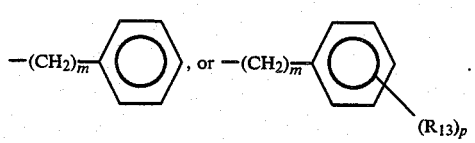

$R_{13}$ is lower alkyl of 1 to 4 carbons, lower alkoxy of 1 to 4 carbons, lower alkylthio of 1 to 4 carbons, chloro, bromo, fluoro, trifluoromethyl, hydroxy, phenyl, phenoxy, phenylthio, or phenylmethyl.

$R_{14}$ is lower alkyl of 1 to 4 carbons, lower alkoxy of 1 to 4 carbons, lower alkylthio of 1 to 4 carbons, chloro, bromo, fluoro, trifluoromethyl or hydroxy.

m is zero, one, two, three, or four.

p is one, two or three provided that p is more than one only if $R_{13}$ or $R_{14}$ is methyl, methoxy, chloro, or fluoro.

$R_{15}$ is hydrogen or lower alkyl of 1 to 4 carbons.

Y is oxygen or sulfur.

$R_{16}$ is lower alkyl of 1 to 4 carbons,

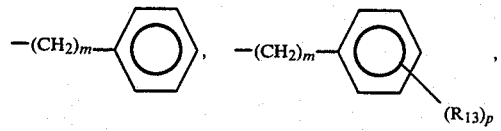

or the $R_{16}$ groups join to complete an unsubstituted 5- or 6-membered ring or said ring in which one or more of the carbons has a lower alkyl of 1 to 4 carbons or a di(lower alkyl of 1 to 4 carbons) substituent.

$R_4$ is hydrogen, lower alkyl,

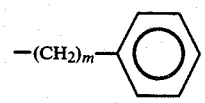

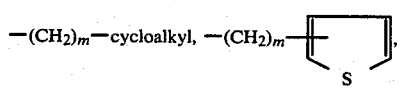

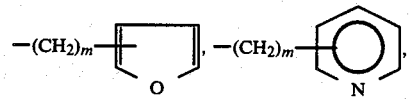

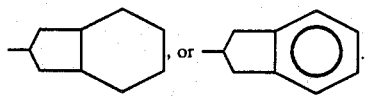

$R_5$ is hydrogen, lower alkyl,

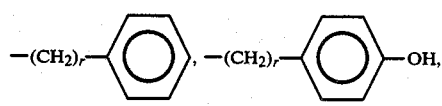

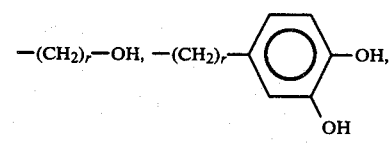

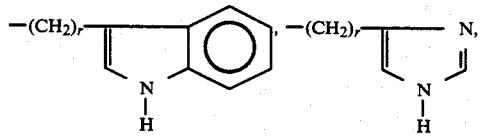

$-(CH_2)_r-NH_2$, $-(CH_2)_r-SH$, $-(CH_2)_r-S-$lower alkyl,

-continued

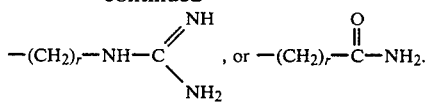, or —(CH$_2$)$_r$—C(=O)—NH$_2$.

r is an integer from 1 to 4.

R$_{19}$ is lower alkyl, benzyl or phenethyl.

R$_{20}$ is hydrogen, lower alkyl, benzyl or phenethyl.

R$_1$ is hydrogen, lower alkyl, halo substituted lower alkyl,

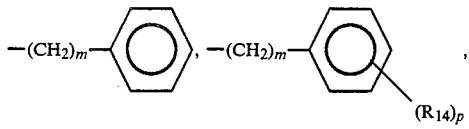

—(CH$_2$)$_m$—cycloalkyl, —(CH$_2$)$_2$—NH$_2$, —(CH$_2$)$_3$—NH$_2$,

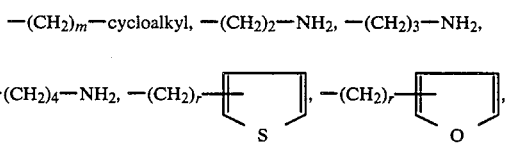

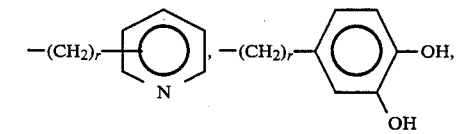

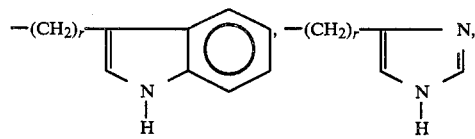

—(CH$_2$)$_r$—SH, —(CH$_2$)$_r$—OH, —(CH$_2$)$_r$—S—lower alkyl,

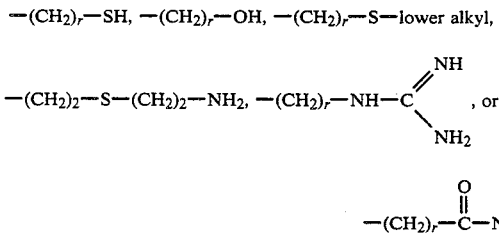

—(CH$_2$)$_r$—C(=O)—NH$_2$ wherein m, R$_{14}$, p and r are as defined above.

R$_3$ is hydrogen, lower alkyl,

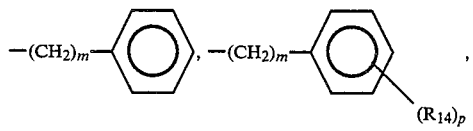

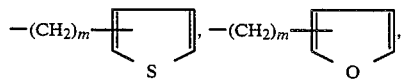

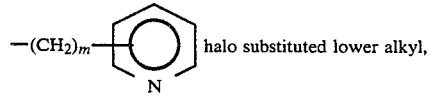 halo substituted lower alkyl,

-continued

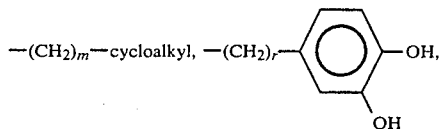

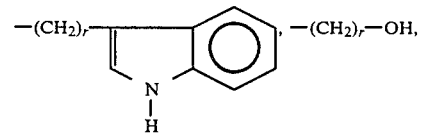

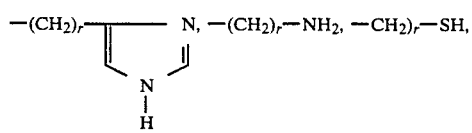

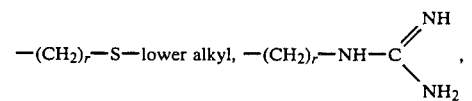

—(CH$_2$)$_r$—S—lower alkyl, 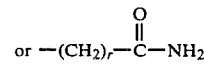,

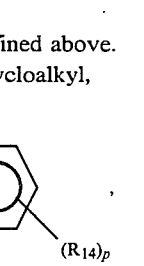

or —(CH$_2$)$_r$—C(=O)—NH$_2$ wherein m, R$_{14}$, p and r are as defined above.

R$_2$ is lower alkyl, —(CH$_2$)$_m$—cycloalkyl,

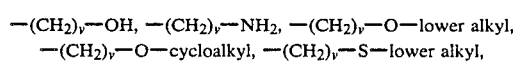

—(CH$_2$)$_v$—OH, —(CH$_2$)$_v$—NH$_2$, —(CH$_2$)$_v$—O—lower alkyl,
—(CH$_2$)$_v$—O—cycloalkyl, —(CH$_2$)$_v$—S—lower alkyl,

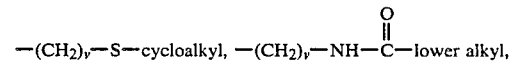

—(CH$_2$)$_v$—S—cycloalkyl, —(CH$_2$)$_v$—NH—C(=O)—lower alkyl,

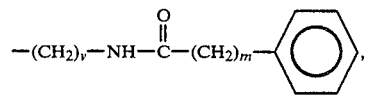,

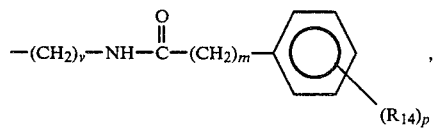

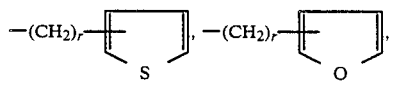

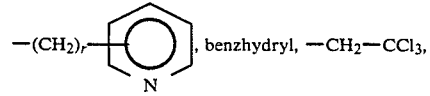, benzhydryl, —CH$_2$—CCl$_3$,

-continued

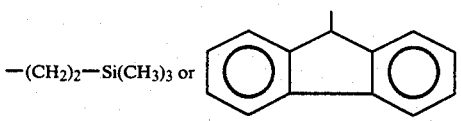

wherein m, $R_{14}$, p and r are as defined above.
v is an integer from 2 to 4.
$R_6$ is hydrogen, lower alkyl, benzyl, benzhydryl,

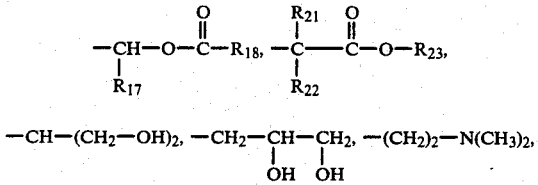

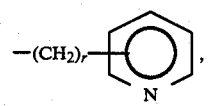

or a salt forming ion.
$R_{17}$ is hydrogen, lower alkyl, cycloalkyl, or phenyl,
$R_{18}$ is hydrogen, lower alkyl, lower alkoxy or phenyl.
$R_{21}$ and $R_{22}$ are independently selected from hydrogen and lower alkyl.
$R_{23}$ is lower alkyl.
$R_{24}$ is hydrogen, lower alkyl,

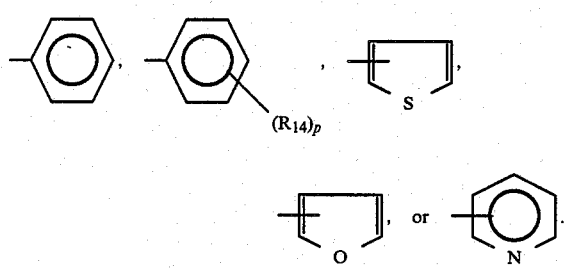

DETAILED DESCRIPTION OF THE INVENTION

This invention in its broadest aspects relates to the ester compounds of formula I, intermediates useful in the preparation of such compounds, to compositions and the method of using such compounds as pharmaceutical agents.

The term lower alkyl used in defining various symbols refers to straight or branched chain radicals having up to seven carbons. The preferred lower alkyl groups are up to four carbons with methyl and ethyl most preferred. Similarly the terms lower alkoxy and lower alkylthio refer to such lower alkyl groups attached to an oxygen or sulfur.

The term cycloalkyl refers to saturated rings of 4 to 7 carbon atoms with cyclopentyl and cyclohexyl being most preferred.

The term halogen refers to chloro, bromo and fluoro.

The term halo substituted lower alkyl refers to such lower alkyl groups described above in which one or more hydrogens have been replaced by chloro, bromo or fluoro groups such as trifluoromethyl, which is preferred, pentafluoro, 2,2,2-trifluoroethyl, chloromethyl, bromomethyl, etc.

The symbols

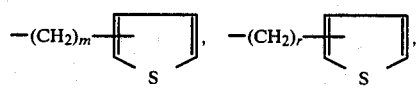

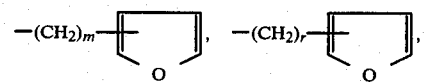

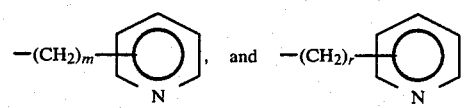

represent that the alkylene bridge is attached to an available carbon atom.

The compounds of formula I are obtained by treating an amine of the formula

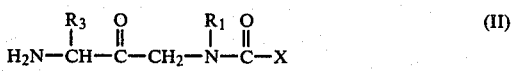

particularly the hydrochloride salt thereof, wherein $R_6$ in the definition of X is an easily removable protecting group such as benzyl, benzhydryl, t-butyl, etc., with phosgene and an amine such as triethylamine followed by treatment with an alcohol of the formula $$R_2-OH \qquad (III)$$

Alternatively, the alcohol of formula III could first be treated with phosgene and the resultant product then treated with the amino intermediate of formula II.

Removal of the $R_6$ protecting group, for example, by hydrogenation when $R_6$ is benzyl, yields the acid products of formula I, i.e., $R_6$ is hydrogen.

The amino intermediate of formula II can be prepared as follows. An amino acid derivative of the formula

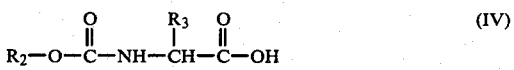

wherein $R_2$ is t-butyl, $-CH_2-CCl_3$, benzhydryl,

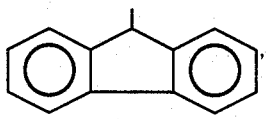

or $-(CH_2)_2-Si(CH_3)_3$ is treated sequentially with isobutylchloroformate and a tertiary base such as N-methylmorpholine followed by reaction with diazomethane and treatment with hydrogen chloride to give

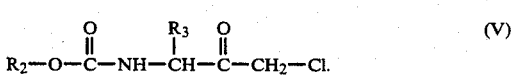

The chloride of formula V is treated with a substituted benzylamine of the formula

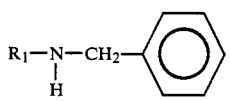 (VI)

to give

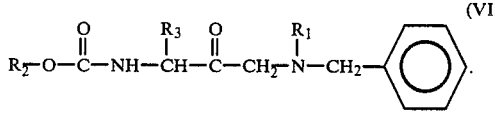 (VII)

Removal of the benzyl protecting group, for example, by hydrogenation gives

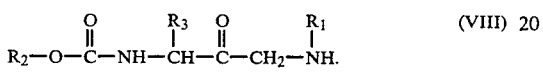 (VIII)

The amine of formula VIII, particularly the p-toluenesulfonic acid salt thereof, is treated with the acid chloride of the formula

 (IX)

in the presence of a base such as triethylamine wherein $R_6$ in the definition of X is an easily removable protecting group to give the product of formula I wherein $R_2$ is t-butyl, —$CH_2$—$CCl_3$, benzhydryl, —($CH_2$)$_2$—Si($CH_3$)$_3$, or

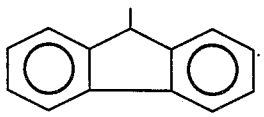

Removal of the t-butyl, benzhydryl, —$CH_2$—$CCl_3$, —($CH_2$)$_2$—Si($CH_3$)$_3$, or

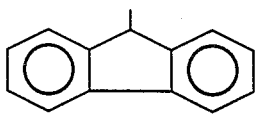

$R_2$ group, for for example by treating with hydrogen chloride when $R_2$ is t-butyl yields the amino intermediate of formula II.

In the above reactions, if $R_1$ is hydrogen then the N-atom is protected, for example by a t-butoxycarbonyl group which can be removed by hydrogenation following completion of the reaction. Similarly, if any or all of $R_1$, $R_3$ and $R_5$ are

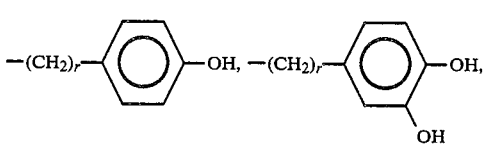

-continued

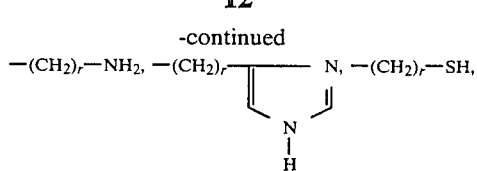

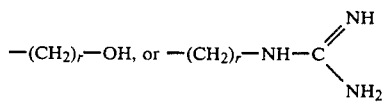

then the hydroxyl, amino, imidazolyl, mercaptan or guanidinyl function should be protected during the reaction. Suitable protecting groups include benzyloxycarbonyl, t-butoxycarbonyl, benzyl, trimethylsilylethylcarbonyl, benzhydryl, trityl, etc., and nitro in the case of guanidinyl. The protecting group is removed by hydrogenation, treatment with acid, or other known methods following completion of the reaction.

The ester products of formula I wherein $R_6$ is

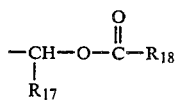

may be obtained by employing the acid chloride of formula IX in the above reactions with such ester group already in place.

The ester products of formula I wherein $R_6$ is

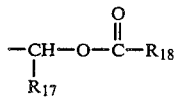

can also be obtained by treating the product of formula I wherein $R_6$ is hydrogen with a molar excess of the compound of the formula

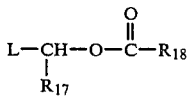 (X)

wherein L is a leaving group such as chlorine, bromine, tolylsulfonyl, etc.

The ester products of formula I wherein $R_6$ is

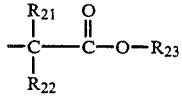

can be prepared by treating the product of formula I wherein $R_6$ is hydrogen with a molar excess of the compound of the formula

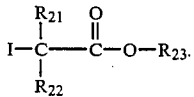 (XI)

The ester products of formula I wherein $R_6$ is —CH—($CH_2$—OH)$_2$ or

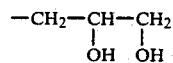

can be prepared by coupling the product of formula I wherein $R_6$ is hydrogen with a molar excess of the compound of the formula

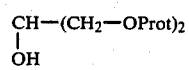 (XII)

or the formula

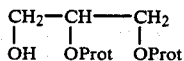 (XIII)

in the presence of a coupling agent such as dicyclohexylcarbodiimide and the optional presence of a catalyst such as dimethylaminopyridine followed by removal of the hydroxyl protecting group.

Similarly, the ester products of formula I wherein $R_6$ is $-(CH_2)_2-N(CH_3)_2$ or

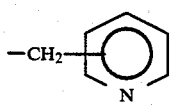

can be prepared by coupling the product of formula I wherein $R_6$ is hydrogen with a molar excess of the compound of formula $$HO-CH_2-CH_2-N-(CH_3)_2 \quad (XIV)$$

or the formula

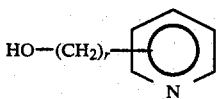 (XV)

in the presence of a coupling agent such as dicyclohexylcarbodiimide and the optional presence of a catalyst such as dimethylaminopyridine.

The products of formula I wherein $R_7$ is amino may be obtained by reducing the corresponding products of formula I wherein $R_7$ is azido.

Preferred compounds of this invention are those of formula I wherein:

X is

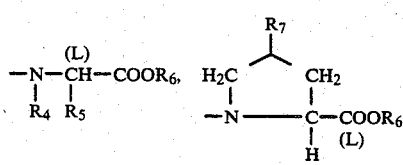

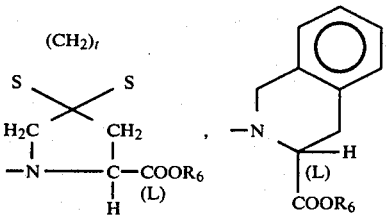

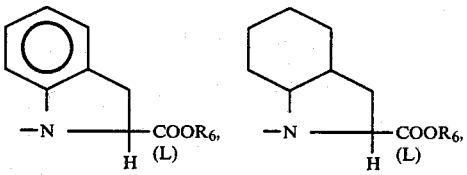

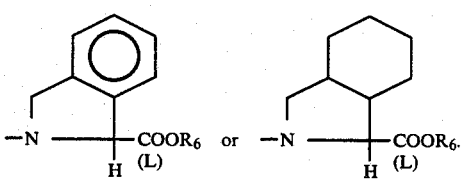

$R_1$ is straight or branched chain lower alkyl of 1 to 4 carbons.

$R_6$ is hydrogen, straight or branched chain lower alkyl of 1 to 4 carbons, or an alkali metal salt ion.

$R_4$ is cyclohexyl or phenyl and $R_5$ is hydrogen.

$R_4$ is hydrogen and $R_5$ is methyl, $-CH_2-CH(CH_3)_2$,

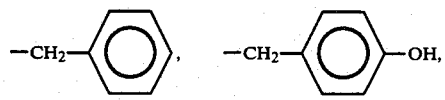

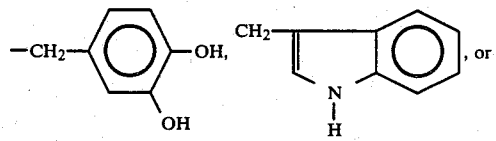

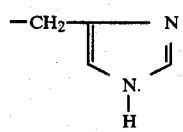

$R_7$ is hydrogen, cyclohexyl, lower alkoxy of 1 to 4 carbons,

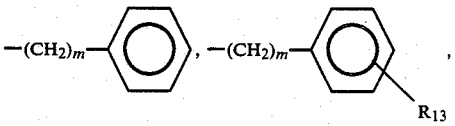

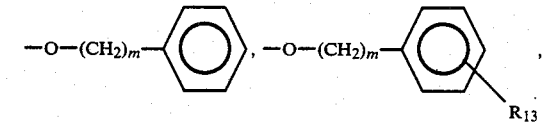

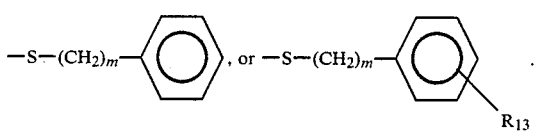

$R_{13}$ is methyl, methoxy, methylthio, Cl, Br, F, or hydroxy.

m is zero, one or two.

t is two or three.

$R_2$ is straight or branched chain lower alkyl of 1 to 4 carbons with the t-butyl compound being preferred as an intermediate,

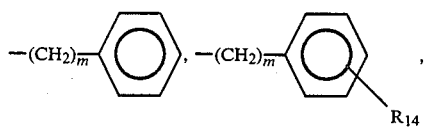

—$(CH_2)_m$—cycloalkyl wherein cycloalkyl is a saturated ring of 5 to 7 carbons, or —$(CH_2)_v$—O—lower alkyl wherein lower alkyl is straight or branched chain of 1 to 4 carbons and v is an integer from 2 to 4.

$R_3$ is straight or branched chain lower alkyl of 1 to 4 carbons,

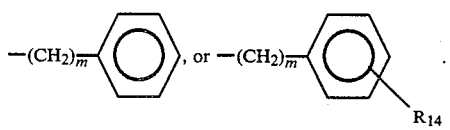

$R_{14}$ is methyl, methoxy, methylthio, Cl, Br, F, or hydroxy.

Most preferred compounds of this invention are those of formula I wherein:

X is

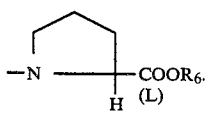

$R_1$ is methyl.

$R_6$ is hydrogen or an alkali metal salt ion.

$R_2$ is methyl, n-butyl, phenyl, cyclohexyl, or —$(CH_2)_2$—O—$CH_3$, especially n-butyl, cyclohexyl, and —$(CH_2)_2$—O—$CH_3$.

$R_3$ is phenylmethyl.

The compounds of formula I wherein $R_6$ is hydrogen form salts with a variety of inorganic or organic bases. The nontoxic, pharmaceutically acceptable salts are preferred, although other salts are also useful in isolating or purifying the product. Such pharmaceutically acceptable salts include alkali metal salts such as sodium, potassium or lithium, alkaline earth metal salts such as calcium or magnesium, and salts derived from amino acids such as arginine, lysine, etc. The salts are obtained by reacting the acid form of the compound with an equivalent of the base supplying the desired ion in a medium in which the salt precipitates or in aqueous medium and then lyophilizing.

The compounds of formula I when $R_3$ is other than hydrogen contain an asymmetric center as represented by the * in formula I. Thus, the compounds of formula I can exist in diastereometric forms or in mixtures thereof. The above described processes can utilize racemates, enantiomers or diastereomers as starting materials. When diastereomeric products are prepared, they can be separated by conventional chromatographic or fractional crystallization methods.

The products of formula I wherein the imino acid ring is monosubstituted give rise to cis-trans isomerism. The configuration of the final product will depend upon the configuration of the $R_7$, $R_8$ and $R_9$ substituent in the starting material of formula IX.

The compounds of formula I, and the pharmaceutically acceptable salts thereof, are hypotensive agents. They inhibit the conversion of the decapeptide angiotensin I to angiotensin II and, therefore, are useful in reducing or relieving angiotensin related hypertension. The action of the enzyme renin on angiotensinogen, a pseudoglobulin in blood plasma, produces angiotensin I. Angiotensin I is converted by angiotensin converting enzyme (ACE) to angiotensin II. The latter is an active pressor substance which has been implicated as the causative agent in several forms of hypertension in various mammalian species, e.g., humans. The compounds of this invention intervene in the angiotensinogen→(renin)→angiotensin I→angiotensin II sequence by inhibiting angiotensin converting enzyme and reducing or eliminating the formation of the pressor substance angiotensin II. Thus by the administration of a composition containing one (or a combination) of the compounds of this invention, angiotensin dependent hypertension in a species of mammal (e.g., humans) suffering therefrom is alleviated. A single dose, or preferably two to four divided daily doses, provided on a basis of about 0.1 to 100 mg., preferably about 1 to 50 mg., per kg. of body weight per day is appropriate the reduce blood pressure. The substance is preferably administered orally but parenteral routes such as the subcutaneous, intrasmuscular, intravenous or intraperitoneal routes can also be employed.

The compounds of this invention can also be formulated in combination with a diuretic for the treatment of hypertension. A combination product comprising a compound of this invention and a diuretic can be administered in an effective amount which comprises a total daily dosage of about 30 to 600 mg., preferably about 30 to 330 mg. of a compound of this invention, and about 15 to 300 mg., preferably about 15 to 200 mg. of the diuretic, to a mammalian species in need thereof. Exemplary of the diuretics contemplated for use in combination of this invention are the thiazide diuretics, e.g., chlorothiazide, hydrochlorothiazide, flumethiazide, hydroflumethiazide, bendroflumethiazide, methyclothiazide, trichloromethiazide, polythiazide or benzthiazide as well as ethacrynic acid, tricrynafen, chlorthalidone, furosemide, musolimine, bumetanide, triamterene, amiloride and spironolactone and salts of such compounds.

The compounds of formula I can be formulated for use in the reduction of blood pressure in compositions such as tablets, capsules or elixirs for oral administration, or in sterile solutions or suspensions for parenteral administration. About 10 to 500 mg. of a compound of formula I is compounded with physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The compounds of formula I wherein X is

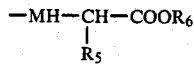

also possess enkephalinase inhibition activity and are useful as analgesic agents. Thus, by the administration of a composition containing one or a combination of such compounds of formula I or a pharmaceutically acceptable salt thereof, pain is alleviated in the mammalian host. A single dose, or preferably two to four divided daily doses, provided on a basis of about 0.1 to about 100 mg. per kilogram of body weight per day, preferably about 1 to about 50 mg., per kilogram per day, produces the desired analgesic activity. The composition is preferably administered orally but parenteral routes such as subcutaneous can also be employed.

The following examples are illustrative of the invention. Temperatures are given in degrees centigrade.

EXAMPLE 1

1-[[[(S)-3-[[(1,1-Dimethylethoxy)carbonyl]amino]-2-oxo-4-phenylbutyl]methylamino]carbonyl]-L-proline, monolithium salt

(a)

(S)-[3-Chloro-2-oxo-1-(phenylmethyl)propyl]carbamic acid, 1,1-dimethylethyl ester To a stirred solution of N-[(1,1-dimethylethoxy)carbonyl]-L-phenylalanine (26.5 g., 100 mmole) in tetrahydrofuran (150 ml.) at −20° is added isobutylchloroformate (13 ml., 100 mmole). N-Methylmorpholine (11 ml., 100 mmole) is then added in drops. The solution is stirred between −15° C. and −20° C. for fifteen minutes and then filtered. Tetrahydrofuran (25 ml.) is used for the washings. The filtrate is added to a cold (ice bath) ethereal solution of diazomethane in drops. After the addition is over, the ice bath is removed, and the reaction mixture is stirred at ambient temperature for 2 hours. Nitrogen is blown over the solution and the volume is reduced to 400 ml. The reaction mixture is then stirred in an ice bath and hydrogen chloride in acetic acid (2N, 55 ml.) is added in drops. After the addition is over, the ice bath is removed and the reaction mixture is stirred for 15 minutes at room temperature. The reaction mixture is evaporated in vacuo and the residue on attempted dissolution in ether affords 6.2 g. of (S)-[3-chloro-2-oxo-1-(phenylmethyl)propyl]carbamic acid, 1,1-dimethylethyl ester; m.p. 104°-105°; $[\alpha]_D^{22} = +20.3°$ (c=2, chloroform). The mother liquor on concentration and after crystallization from ether/hexane gives an additional 17.65 g. of product.

(b)

(S)-[3-[Methyl(phenylmethyl)amino]-2-oxo-1-(phenylmethyl)propyl]carbamic acid 1,1-dimethylethyl ester, p-toluenesulfonate salt A solution of (S)-[3-chloro-2-oxo-1-(phenylmethyl)propyl]carbamic acid, 1,1-dimethylethyl ester (6.43 g., 21.6 mmole), sodium bicarbonate (2.17 g., 25.9 mmole), sodium iodide (1.62 g., 11.0 mmole) and benzylmethylamine (2.76 ml., 2.14 mmole) in dimethylformamide (60 ml.) is stirred at room temperature for 4 hours. The resulting solution is concentrated and partitioned between ether and water. The ether layer is washed with water (twice) and extracted with 1N hydrochloric acid (five times). The combined extracts are made basic using sodium bicarbonate and extracted with ethyl acetate. The ethyl acetate extracts are dried (MgSO₄) and concentrated. The crude crystalline residue is dissolved in ether and a solution of p-toluenesulfonic acid (3.0 g., 28 mmole) in ethyl acetate is added. The resulting pink crystals are triturated with hot ethyl acetate and collected to give 6.5 g. of (S)-[3-[methyl(phenylmethyl)amino]-2-oxo-1-(phenylmethyl)propyl]carbamic acid, 1,1-dimethylethyl ester, p-toluenesulfonate salt as a white solid; m.p. 150°-152°.

(c)

(S)-[3-(Methylamino)-2-oxo-1-(phenylmethyl)propyl]-carbamic acid, 1,1-dimethylethyl ester, hydrochloride salt A mixture of p-toluenesulfonate salt product from part (b) (6.5 g., 11.7 mmole) and palladium hydroxide (20%) in methanol is hydrogenated at atmospheric pressure and room temperature for 1.5 hours. The resulting solution is filtered, concentrated, and triturated with ether to give 4.75 g. of a white crystalline solid. A portion of this material is partitioned between ethyl acetate and 10% sodium bicarbonate. The organic layer is treated with hydrochloric acid/ether to give the crude hydrochloride salt as blue-green solid. Recrystallization from methanol/ether gives (S)-[3-(methylamino)-2-oxo-1-(phenylmethyl)propyl]carbamic acid, 1,1-dimethylethyl ester, hydrochloride salt; m.p. 164°-169°.

(d)

1-[[[(S)-3-[[(1,1-Dimethylethoxy)carbonyl]amino]-2-oxo-4-phenylbutyl]methylamino]carbonyl]-L-proline, phenylmethyl ester N-Methylmorpholine (0.46 ml., 4.2 mmole) is added to a stirring suspension of L-proline, phenylmethyl ester, hydrochloride salt (0.39 g., 1.6 mmole) in methylene chloride (dry, distilled) at −40° followed by phosgene in benzene (approximately 1M, 2.5 ml., 2.5 mmole). The mixture is stirred at −30° for one hour. The ice bath is removed and the mixture is stirred for an additional hour. The mixture is then concentrated in vacuo and diluted with methylene chloride. (S)-[3-(Methylamino)-2-oxo-1-(phenylmethyl)propyl]carbamic acid, 1,1-dimethylethyl ester, hydrochloride salt (0.34 g., 1.0 mmole) is added to the solution and the mixture is stirred overnight. The resulting solution is diluted with methylene chloride and washed with 1N hydrochloric acid and 10% sodium bicarbonate, dried (MgSO₄) and concentrated. The crude product (0.61 g.) is combined with material from a previous run (0.56 g.) and chromatographed on LPS-1 silica gel using hexane:ethyl acetate (2:1) as the eluant. The combined fractions are re-chromatographed on LPS-1 using ether:ethyl acetate (10:1) as eluent. Fractions containing the desired product ($R_f$=0.43, hexane:ethyl acetate, 1:1) are combined and concentrated to give 0.26 g. of 1-[[[(S)-3-[[(1,1-dimethylethoxy)carbonyl]amino]-2-oxo-4-phenylbutyl]methylamino]carbonyl]-L-proline, phenylmethyl ester.

(e)

1-[[[(S)-3-[[(1,1-Dimethylethoxy)carbonyl]amino]-2-oxo-4-phenylbutyl]methylamino]carbonyl]-L-proline, monolithium salt A solution of the phenylmethyl ester product from part (d) (0.26 g., 0.5 mmole) and palladium hydroxide (20%) in ethyl acetate (25 ml.) is hydrogenated at atmospheric pressure and room temperature for 1.5 hours. The resulting solution is filtered and concentrated. The residue is treated with 0.1M lithium carbonate (2.5 ml., 0.5 mmole of Li) and lyophilized to give 0.15 g. of 1-[[[(S)-3-[[(1,1-dimethylethoxy)carbonyl]amino]-2-oxo-4-phenylbutyl]methylamino]carbonyl]-L-proline, monolithium salt as a white solid; m.p. (130) 132°–140°; $[\alpha]_D = -26°$ (c=0.8%, methanol). TLC (silica gel; toluene:acetic acid, 4:1) $R_f = 0.17$.

Anal. Calc'd. for $C_{22}H_{30}N_3O_6Li \cdot 1.5\ H_2O$: C, 56.65; H, 7.13; N, 9.01. Found: C, 56.56; H, 6.71; N, 8.93.

EXAMPLE 2

1-[[[(S)-3-[(Methoxycarbonyl)amino]-2-oxo-4-phenylbutyl]methylamino]carbonyl]-L-proline, monolithium salt (a)

1-[[[(S)-3-Amino-2-oxo-4phenylbutyl]methylamino]carbonyl]-L-proline, phenylmethyl ester A solution of 1-[[[(S)-3-[[(1,1-dimethylethoxy)carbonyl]amino]-2-oxo-4-phenylbutyl]methylamino]carbonyl]-L-proline, phenylmethyl ester (7.12 g., 13.6 mmole) is stirred in a saturated solution of hydrochloric acid/ethyl acetate for one hour. The resulting precipitate is collected and washed with ethyl acetate to give 5.63 g. of 1-[[[(S)-3-amino-2-oxo-4-phenylbutyl]methylamino]carbonyl]-L-proline, phenylmethyl ester; m.p. 174°–175°; $[\alpha]_D^{25} = +16.20°$. TLC (silica gel; chloroform:methanol:acetic acid, 4:1:1) $R_f = 0.60$.

(b)

1-[[[(S)-3-[(Methoxycarbonyl)amino]-2-oxo-4-phenylbutyl]methylamino]carbonyl]-L-proline, phenylmethyl ester A solution of the phenylmethyl ester product from part (a) (0.89 g., 2.0 mmole) in methylene chloride (dry, distilled) and phosgene in benzene (1.2M, 3.0 ml., 3.6 mmole) is cooled at −20°. N-Methylmorpholine (1.1 ml., 10.0 mmole) in methylene chloride (10 ml.) is added over several minutes and the resulting solution is stirred at −20° for 10 minutes, and at room temperature for an additional 15 minutes. The mixture is concentrated in vacuo and the residue is dissolved in methylene chloride and methanol (1 ml.) and stirred at room temperature for 5.5 hours. The resulting solution is diluted with methylene chloride, washed with 1N hydrochloric acid and 10% sodium bicarbonate, dried (MgSO₄) and concentrated. The crude product is chromatographed on LPS-1 silica gel using ether as the eluant. Fractions containing the desired product ($R_f=0.15$, ether) are combined and concentrated to give 0.49 g. of 1-[[[(S)-3-[(methoxycarbonyl)amino]-2-oxo-4-phenylbutyl]methylamino]carbonyl]-L-proline, phenylmethyl ester as a white foam.

(c)

1-[[[(S)-3-[(Methoxycarbonyl)amino]-2-oxo-4-phenylbutyl]methylamino]carbonyl]-L-proline, monolithium salt A mixture of the phenylmethyl ester product from part (b) (0.45 g., 0.93 mmole) and palladium hydroxide (20%) in ethyl acetate (10 ml.) is hydrogenated at atmospheric pressure and room temperature for 3 hours. The resulting solution is filtered and concentrated. The residue is treated with 0.1M lithium carbonate (4.45 ml.) and chromatographed on HP-20 using a methanol in water gradient (0→100%). Fractions containing the desired product are combined and concentrated to remove methanol and lyophilized to give 0.19 g of 1-[[[(S)-3-[(methoxycarbonyl)amino]-2-oxo-4-phenylbutyl]methylamino]carbonyl]-L-proline, monolithium salt as a white solid; m.p. (100) 112°–135° (dec.); $[\alpha]_D^{25} = -24°$ (c=1%, methanol). TLC (silica gel; toluene:acetic acid, 4:1) $R_f = 0.18$.

Anal. calc'd. for $C_{19}H_{24}N_3O_6Li \cdot 0.82\ H_2O$: C, 55.37; H, 6.27; N, 10.20. Found: C, 55.37; H, 6.10; N, 10.24.

EXAMPLE 3

1-[[[(S)-3-[(butoxycarbonyl)amino]-2-oxo-4-phenylbutyl]methylamino]carbonyl]-L-proline, monolithium salt 1-[[[(S)-3-[(Butoxycarbonyl)amino]-2-oxo-4-phenylbutyl]methylamino]carbonyl]-L-proline, phenylmethyl ester Phosgene (12% in benzene, 3.0 ml., 3.6 mmole) is added in one portion to a solution of 1-[[[(S)-3-amino-2-oxo-4-phenylbutyl]methylamino]carbonyl]-L-proline, phenylmethyl ester (0.89 g., 2.0 mmole) in methylene chloride (10 ml.) at −20° under argon. A solution of N-methylmorpholine (1.1 ml., 10 mmole) in methylene chloride (10 ml.) is then added dropwise over 10 minutes. The resulting solution is stirred at −20° for ten minutes and at room temperature for an additional 15 minutes. The mixture is concentrated in vacuo, dissolved in methylene chloride (10 ml.) and n-butyl alcohol (3 ml.) and stirred at room temperature overnight. The resulting solution is diluted with methylene chloride, washed with 1N hydrochloric acid and 10% sodium bicarbonate, dried (MgSO₄), and concentrated to a yellow oil. The crude product is chromatographed on LPS-1 silica gel using ether as the eluant. Fractions containing the desired product ($R_f=0.51$, ether) are combined and concentrated to give 0.56 g. of 1-[[[(S)-3-[(butoxycarbonyl)amino]-2-oxo-4-phenylbutyl]methylamino]carbonyl]-L-proline, phenylmethyl ester as a clear oil.

(b)

1-[[[(S)-3-[(Butoxycarbonyl)amino]-2-oxo-4-phenylbutyl]methylamino]carbonyl]-L-proline, monolithium salt A mixture of the phenylmethyl ester product from part (a) (0.5 g., 0.95 mmole) and palladium hydroxide (20%) in ethyl acetate (15 ml.) is hydrogenated at room temperature and atmospheric pressure for 2.5 hours. The resulting solution is filtered and concentrated. The residue is treated with 0.1M lithium carbonate (5 ml.) and chromatographed on HP-20 using a 0–50% aqueous methanol elution gradient. Fractions containing the desirted product are combined, concentrated to remove methanol, and lyophilized to give 0.18 g. of 1-[[[(S)-3-

[(butoxycarbonyl)amino]-2-oxo-4-phenylbutyl]methylamino]carbonyl]-L-proline, monolithium salt as a white solid; m.p. (90) 100°–110°; $[\alpha]_D = -24°$ (c=1%, methanol). TLC (silica gel; toluene:acetic acid, 4:1) $R_f=0.30$.

Anal. calc'd. for $C_{22}H_{20}N_3O_6Li.0.3\ H_2O$ C, 59.36; H, 6.93; N, 9.44. Found: C, 59.36; H, 6.91; N, 9.33.

EXAMPLE 4

(S)-1-[[Methyl[2-oxo-3-[(phenoxycarbonyl)amino]-4-phenylbutyl]amino]carbonyl]-L-proline, monolithium salt (a)

(S)-1-[[Methyl[2-oxo-3-[(phenoxycarbonyl)amino]-4-phenylbutyl]amino]carbonyl]-L-proline, phenylmethyl ester Phosgene (1.2M solution in benzene, 3.0 ml., 3.6 mmole) is added to a stirring suspension of 1-[[[(S)-3-amino-2-oxo-4-phenylbutyl]methylamino]carbonyl]-L-proline, phenylmethyl ester (0.89 g., 2.0 mmole) in methylene chloride at −40° under argon. A solution of N-methylmorpholine in methylene chloride (1.1 ml., 10.0 mmole) is added dropwise over a period of 5 minutes. Stirring is continued for 10 minutes at −40° to −20° and for 20 minutes after removal of the dry ice bath. The mixture is concentrated in vacuo and diluted with methylene chloride. Phenol (0.38 g., 4.0 mmole) is added in one portion and the resulting mixture is stirred at room temperature under argon overnight. The reaction mixture is diluted with methylene chloride and washed consecutively with water, 1N hydrochloric acid, and 10% sodium bicarbonate. The organic phase is dried (MgSO4) and concentrated to a yellow-orange oil. The crude product is chromatographed on LPS-1 silica gel using an elution gradient of hexane:ethyl acetate (3:1→1:1). Fractions containing the desired product ($R_f=0.3$, hexane:ethyl acetate, 1:1) are combined and concentrated to give 0.46 g. of (S)-1-[[methyl[2-oxo-3-[(phenoxycarbonyl)amino]-4-phenylbutyl]amino]carbonyl]-L-proline, phenylmethyl ester as a clear oil.

(b)

(S)-1-[[Methyl[2-oxo-3-[(phenoxycarbonyl)amino]-4-phenylbutyl]amino]carbonyl]-L-proline, monolithium salt A suspension of the phenylmethyl ester product from part (a) (0.46 g., 0.85 mmole) and palladium hydroxide (20%) in ethyl acetate is hydrogenated at room temperature and atmospheric pressure for 1.5 hours. The reaction mixture is filtered and concentrated. The residue is dissolved in methanol and treated with 0.1M lithium carbonate (3.5 ml., 0.7 mmole of Li). The product is chromatographed on HP-20 using an aqueous acetonitrile gradient (10%→100% acetonitrile). Fractions containing the desired product are combined and concentrated to give 0.18 g. of (S)-1-[[methyl[2-oxo-3-[(phenoxycarbonyl)amino]-4-phenylbutyl]amino]carbonyl]-L-proline, monolithium salt as a white solid; m.p. 110°–122°; $[\alpha]_D^{25} = -21°$ (c=1%, water). TLC (silica gel; toluene:acetic acid, 4:1) $R_f=0.20$.

Anal. calc'd for $C_{24}H_{26}N_3O_6Li.1.0\ H_2O$: C, 60.38; H, 5.91; N, 8.80. Found: C, 60.49; H, 5.76; N, 9.09.

EXAMPLE 5

1-[[[(S)-3-[[(Cyclohexyloxy)carbonyl]amino]-2-oxo-4-phenylbutyl]methylamino]carbonyl]-L-proline, monolithium salt (a)

1-[[[(S)-3-[[(Cyclohexyloxy)carbonyl]amino]-2-oxo-4-phenylbutyl]methylamino]carbonyl]-L-proline, phenylmethyl ester Phosgene (1.2M solution in benzene, 3.0 ml., 3.6 mmole) is added to a stirring suspension of 1-[[[(S)-3-amino-2-oxo-4-phenylbutyl]methylamino]carbonyl]-L-proline, phenylmethyl ester (0.89 g., 2.0 mmole) in methylene chloride at −40° under argon. A solution of N-methylmorpholine (1.1 ml., 10.0 mmole) in methylene chloride is added dropwise over a period of five minutes. Stirring is continued for 15 minutes at −40° and for one hour as the mixture warms slowly to room temperature. The resulting mixture is concentrated in vacuo. The residue is dissolved in cyclohexanol (10 ml.), stirred at room temperature for two hours and at 80° overnight. The solution is concentrated, diluted with chloroform and washed consecutively with water, 1N hydrochloric acid, and 10% sodium bicarbonate in water. The organic phase is dried (MgSO4) and concentrated. Chromatography of the crude product on LPS-1 silica gel using a hexane:ethyl acetate gradient (30%→100% ethyl acetate) gives 0.58 g. of 1-[[[(S)-3-[[(cyclohexyloxy)carbonyl]amino]-2-oxo-4-phenylbutyl]methylamino]carbonyl]-L-proline, phenylmethyl ester as a clear oil.

(b) 1-[[[(S)-3-[[(Cyclohexyloxy)carbonyl]amino]-2-oxo-4-phenylbutyl]methylamino]carbonyl]-L-proline, monolithium salt A suspension of the phenylmethyl ester product from part (a) (0.58 g., 1.06 mmole) and palladium hydroxide (20% in ethyl acetate is stirred under hydrogen at room temperature and atmospheric pressure for 2.5 hours. The resulting mixture is filtered and concentrated. The residue is treated with 0.1M lithium carbonate (4.3 ml., 0.86 mmole Li) and chromatographed on HP-20 using aqueous methanol (0→100%) as eluant. Fractions containing the desired product are combined, concentrated, and lyophilized to give 0.19 g. of 1-[[[(S)-3-[[(cyclohexyloxy)carbonyl]amino]-2-oxo-4-phenylbutyl]methylamino]carbonyl]-L-proline, monolithium salt as a white solid; m.p. 110°–124°; $[\alpha]_D^{25} = -14°$ (c=1%, water). TLC (silica gel; toluene:acetic acid, 4:1) $R_f=0.25$.

Anal. calc'd. for $C_{24}H_{31}N_3O_6Li.0.95\ H_2O$: C, 59.86; H, 6.89; N, 8.73. Found: C, 59.86; H, 6.76; N, 8.40.

EXAMPLE 6

1-[[[(S)-3-[[(2-Methoxyethoxy)carbonyl]amino]-2-oxo-4-phenylbutyl]methylamino]carbonyl]-L-proline, monolithium salt (a)

1-[[[(S)-3-[[(2-Methoxyethoxy)carbonyl]amino]-2-oxo-4-phenylbutyl]methylamino]carbonyl]-L-proline, phenylmethyl ester Phosgene (1.2M solution in benzene, 1.5 ml., 1.8 mmole) is added to a solution of 1-[[[(S)-3-amino-2-oxo-4-phenylbutyl]methylamino]carbonyl]-L-proline, phenylmethyl ester (460 mg., 1 mmole) in methylene chloride (10 ml.) at −30° followed by N-methylmorpholine (0.56 ml., 5 mmole) in methylene chloride (5 ml.). When addition is complete (10 minutes), the mixture is allowed to warm to room temperature over 45 minutes. The solution is then concentrated and the residue is redissolved in 2-methoxyethanol (1.5 ml.). The mixture is then stirred overnight at room temperature. The resulting solution is diluted with ethyl acetate and washed sequentially with 1N hydrochloric acid and 10% sodium bicarbonate, dried (MgSO₄), and concentrated to give 250 mg. of a yellow oil. Preparation layer chromatography of the oil (silica gel, ethyl acetate) gives 150 mg. of 1-[[[(S)-3-[[(2-methoxyethoxy)carbonyl]amino]-2-oxo-4-phenylbutyl]methylamino]carbonyl]-L-proline, phenylmethyl ester as the major product.

(b) 1-[[[(S)-3-[[(2-Methoxyethoxy)carbonyl]amino]-2-oxo-2-phenylbutyl]methylamino]carbonyl]-L-proline, monolithium salt A mixture of the phenylmethyl ester product from part (a) (420 mg., 0.80 mmole) and palladium hydroxide (20%, 50 mg.) in ethyl acetate (10 ml.) is hydrogenated for 5 hours at one atmosphere and room temperature. The mixture is then filtered and concentrated to give 310 mg. of a colorless foam. This foam is dissolved in methanol and lithium carbonate solution (3.5 ml. of 0.2N, 7 mmole) is added. The mixture is concentrated and the residue is chromatographed on HP-20 using a water to methanol elution gradient. Fractions containing the desired product are concentrated and lyophilized to give 1-[[[(S)-3-[[(2-methoxyethoxy)carbonyl]amino]-2-oxo-4-phenylbutyl]methylamino]carbonyl]-L-proline, monolithium salt as a white powder; m.p. approximately 100°–110° (sinters at 65°–70°, no sharp m.p.); $[\alpha]_D^{25} = -34°$ (c=0.5, methanol). TLC (silica gel; toluene:acetic acid, 4:1) $R_f$=0.35.

Anal. calc'd. for $C_{21}H_{28}N_3O_7Li \cdot 2.4 H_2O$: C, 51,96; H, 6.81; N, 8.65. Found: C, 51.96; H, 6.88; N, 8.58.

EXAMPLES 7–35

Following the procedure of Examples 2 to 6, the amine shown in Col. I is treated with phosgene and then reacted with the alcohol shown in Col. II to yield the product shown in Col. III. Removal of the $R_6$ ester group yields the corresponding acid product.

Col. I

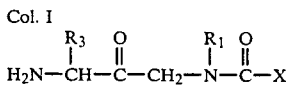

Col. II

Col. III

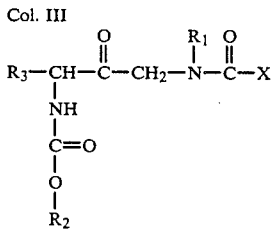

| Example | $R_3$ | $R_2$ | $R_1$ | X |
|---|---|---|---|---|
| 7 | PhCH$_2$— | PhCH$_2$— | —CH$_3$ | –N(CH$_2$CH(SPh)CH$_2$)–CH(COOCH$_2$Ph)(H) (L) |
| 8 | Ph— | CyCH$_2$— | —CH$_3$ | –N(CH$_2$CH(Cy)CH$_2$)–CH(COOCH$_2$Ph)(H) (L) |
| 9 | (2-pyridyl)CH$_2$— | H$_3$C–C(=O)–NH–CH$_2$— | —CH$_3$ | –N(CH$_2$CH(CH$_2$Ph)CH$_2$)–CH(COOCH$_2$Ph)(H) (L) |
| 10 | (2-thienyl)CH$_2$— | Ph–C(=O)–NH–CH$_2$— | —CH$_3$ | –N(CH$_2$CH(OCH$_2$-4-F-C$_6$H$_4$)CH$_2$)–CH(COOCH$_2$Ph)(H) (L) |

-continued

| Example | R₃ | R₂ | R₁ | X |
|---|---|---|---|---|
| 11 | (indol-3-yl)-CH₂— | (pyridin-2-yl)-CH₂— | —CH₃ | −N(CH₂CH(Ph)CH₂)−CH(COOCH₂Ph)(H) (L) |
| 12 | (4-methoxyphenyl)-CH₂— | (furan-2-yl)-CH₂— | —CH₃ | −N(CH₂CH(CH₃)CH₂)−CH(COOCH₂Ph)(H) (L) |
| 13 | Ph-(CH₂)₂— | H₃C—(CH₂)₅— | —CH₃ | −N(CH₂CCl₂CH₂)−CH(COOCH₂Ph)(H) (L) |
| 14 | Ph-CH₂— | Ph-CH₂-O-C(=O)-NH-(CH₂)₄— | —CH₃ | −N(CH₂C(S-S)CH₂)−CH(COOCH₂Ph)(H) (L) |
| 15 | Ph-CH₂— | Ph-CH₂-O-(H₂C)₂— | —CH₃ | 1,2,3,4-tetrahydroisoquinoline-3-carboxylic acid benzyl ester (L) |

-continued

| Example | R₃ | R₂ | R₁ | X |
|---|---|---|---|---|
| 16 | -CH₂-C₆H₅ | 2-thienyl-CH₂- | -CH₃ | N-(2-benzyl)phenyl-CH(COOCH₂C₆H₅)- (L), H |
| 17 | -CH₂-C₆H₅ | 2-furyl-CH₂- | -CH₃ | N-(2-benzyl)phenyl-CH(COOCH₂C₆H₅)- (L), H |
| 18 | -CH₂-C₆H₅ | H₃C-(CH₂)₃- | -CH₂-C₆H₅ | N-CH₂CH₂S-CH(COOCH₂C₆H₅)- (L), H |
| 19 | -CH₂-C₆H₅ | cyclohexyl | -CH₂-(indol-2-yl)-NH | N-(1,4-dioxaspiro)CH(COOCH₂C₆H₅)- (L), H |
| 20 | -CH₂-C₆H₅ | H₃C-(CH₂)₃- | -(CH₂)₂-NH-C(O)-O-CH₂-C₆H₅ | N-butyl-CH(COOCH₂C₆H₅)- (L), H |

-continued

| Example | R₃ | R₂ | R₁ | X |
|---|---|---|---|---|
| 21 | $C_6H_5-CH_2-$ | cyclohexyl | $-CH_2-O-CH_2-C_6H_5$ | $-N$(2-cyclohexyl-CH₂-)CH(COOCH₂C₆H₅)(L)/H |
| 22 | $C_6H_5-CH_2-$ | $H_5C_2-O-(H_2C)_2-$ | $-CH_3$ | $-N=N-C(CH_3)-CH_2-$ CH(COOCH₂C₆H₅)(L)/H |
| 23 | $C_6H_5-CH_2-$ | cyclohexyl | $-(CH_2)_3-NH-C(=NH)-NH-NO_2$ | $-N$(cyclohexyl)CH(COOCH₂C₆H₅)(L)/H |
| 24 | $C_6H_5-CH_2-$ | $H_3C-(CH_2)_3-$ | $-CH_2-C_6H_4-OCH_2-C_6H_5$ | $-N$(2-(cyclopentyl-CH₂-))CH(COOCH₂C₆H₅)(L)/H |
| 25 | $C_6H_5-CH_2-$ | $C_6H_5-$ | $-CH_2-C_6H_3(OCH_2C_6H_5)(OCH_2-)$ | $-N$(2-cyclopentyl-)CH(COOCH₂C₆H₅)(L)/H |

-continued

| Example | R₃ | R₂ | R₁ | X |
|---|---|---|---|---|
| 26 | PhCH₂— | H₅C₂— | —CH₃ | pyrrolidine-N—CH₂—CH(COOCH₂Ph)(H) (L) |
| 27 | PhCH₂— | H₃C—O—(CH₂)₂— | —CH₃ | —N(Ph)—CH₂—COOCH₂Ph |
| 28 | PhCH₂— | H₃C—(CH₂)₂— | —CH₃ | —N(C₆H₁₁)—CH₂—COOCH₂Ph |
| 29 | PhCH₂— | PhCH₂— | —CH₃ | —NH—CH(CH₃)—COOCH₂Ph (L) |
| 30 | PhCH₂— | H₃C—(CH₂)₃— | —CH₃ | —NH—CH(CH₂—CH(CH₃)₂)—COOCH₂Ph (L) |
| 31 | PhCH₂— | H₃C—(CH₂)₃— | —CH₃ | —NH—CH(CH₂Ph)—COOCH₂Ph (L) |

-continued

| Example | R₃ | R₂ | R₁ | X |
|---|---|---|---|---|
| 32 | PhCH₂— | cyclohexyl | —C₂H₅ | —NH—CH(L)(CH₂Ph)—COOCH₂—CH₂—CH=N—CH₂Ph |
| 33 | PhCH₂— | H₃C—(CH₂)₃— | —CH₃ | —N—CH(CH₂(CH₂)₃CH₃)—C(O)—C(H)(L)(CH(CH₃)₂)—COOC—C₂H₅ (O) |
| 34 | PhCH₂— | cyclohexyl | —CH₃ | —N—CH(CH₂SPh)—C(O)—C(H)(L)(cyclohexyl)—COOC—C₂H₅ (O) |
| 35 | PhCH₂— | H₃C—(CH₂)₃— | —CH₃ | —N—CH(CH₂-cyclohexyl)—C(O)—C(H)(L)(CH(CH₃)₂)—COOC—C₂H₅ (O) |

The $R_2$ protecting groups shown in Examples 14 and 15, the $R_1$ protecting groups shown in Examples 20, 21, 23, 24 and 25, and the $R_5$ protecting group shown in Example 32 are removed as the last step in the synthesis. The $R_6$ ester groups shown in Examples 33 to 35 are not removed.

EXAMPLE 36

1000 tablets each containing the following ingredients

| | |
|---|---|
| 1-[[[(S)—3-[(Methoxycarbonyl)- amino]-2-oxo-4-phenylbutyl]- methylamino]carbonyl]-L—proline, monolithium salt | 100 mg. |
| Cornstarch | 50 mg. |
| Gelatin | 7.5 mg. |
| Avicel(microcrystalline cellulose) | 25 mg. |
| Magnesium stearate | 2.5 mg. |
| | 185 mg. | are prepared from sufficient bulk quantities by mixing the 1-[[[(S)-3-[(methoxycarbonyl)amino]-2-oxo-4-phenylbutyl]methylamino]carbonyl]-L-proline, monolithium salt, and cornstarch with an aqueous solution of the gelatin. The mixture is dried and ground to a fine powder. The Avicel and then the magnesium stearate are admixed with granulation. This mixture is then compressed in a tablet press to form 1000 tablets each containing 100 mg. of active ingredient.

In a similar manner, tablets containing 100 mg. of the product of any of Examples 1 and 3 to 35 can be prepared.

A similar procedure can be employed to form tablets containing 50 mg. of active ingredient.

EXAMPLE 37

Two piece #1 gelatin capsules each containing 50 mg. of 1-[[[(S)-3-[(butoxycarbonyl)amino]-2-oxo-4-phenylbutyl]methylamino]carbonyl]-l-proline, monolithium salt are filled with a mixture of the following ingredients

| | |
|---|---|
| 1-[[[(S)—3-[(Butoxycarbonyl)amino]- 2-oxo-4-phenylbutyl]methylamino]- carbonyl]-L—proline, monolithium salt | 50 mg. |
| Magnesium stearate | 7 mg. |
| Lactose | 193 mg. |
| | 250 mg. |

In a similar manner capsules containing 50 mg. of the product of any of Examples 1, 2, and 4 to 35 can be prepared.

EXAMPLE 38

An injectable solution is prepared as follows:

| | |
|---|---|
| (S)—1-[[Methyl[2-oxo-3- [(phenoxycarbonyl)amino]-4-phenyl- butyl]amino]carbonyl]-L—proline, monolithium salt | 500 g. |
| Methyl paraben | 5 g. |
| Propyl paraben | 1 g. |
| Sodium chloride | 25 g. |
| Water for injection | 5 l |

The active substance, preservatives, and sodium chloride are dissolved in 3 liters of water for injection and then the volume is brought up to 5 liters. The solution is filtered through a sterile filter and aseptically filled into presterilized vials which are closed with presterilized rubber closures. Each vial contains 5 ml. of solution in a concentration of 100 mg. of active ingredient per ml. of solution for injection.

In a similar manner, an injectable solution containing 100 mg. of active ingredient per ml. of solution can be prepared for the product of any of Examples 1 to 3 and 5 to 35.

EXAMPLE 39

100 tablets each containing the following ingredients

| | |
|---|---|
| 1-[[[(S)—3-[[(Cyclohexyloxy)- carbonyl]amino]-2-oxo-4-phenyl- butyl]methylamino]carbonyl]-L— proline, monolithium salt | 100 mg. |
| Avicel | 100 mg. |
| Hydrochlorthiazide | 12.5 mg. |
| Lactose | 113 mg. |
| Cornstarch | 17.5 mg. |
| Stearic acid | 7 mg. |
| | 350 mg. | are prepared from sufficient bulk quantities by slugging the 1-[[[(S)-3-[[(cyclohexyloxy)carbonyl]amino]-2-oxo-4-phenylbutyl]methylamino]carbonyl]-L-proline, monolithium salt, Avicel, and a portion of the stearic acid. The slugs are ground and passed through a #2 screen, then mixed with the hydrochlorothiazide, lactose, cornstarch, and remainder of the stearic acid. The mixture is compressed into 350 mg. capsule shaped tablets in a tablet press. The tablets are scored for dividing in half.

In similar manner, tablets can be prepared containing 100 mg. of the product of any of Examples 1 to 4 and 6 to 35.

What is claimed is:

1. A compound of the formula $$R_3-CH(-NH-C(=O)-O-R_2)-C(=O)-CH_2-N(R_1)-C(=O)-X$$

including a pharmaceutically acceptable salt thereof wherein:

X is $$-N(-CH_2-CH_2-CH(R_7)-CH_2-)-C(H)(L)-COOR_6,$$
$$-N(-CH_2-CH_2-C(CH_2-R_8)(CH_2-)-)-C(H)(L)-COOR_6,$$
$$-N(-CH_2-CH_2-C(R_9)(CH_2-)-CH_2-)-C(H)(L)-COOR_6,$$
$$-N(-CH_2-CH_2-C(R_{10})(R_{10})-CH_2-)-C(H)(L)-COOR_6, \text{ or}$$

-continued
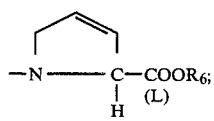
$R_7$ is hydrogen, lower alkyl, halogen, hydroxy,
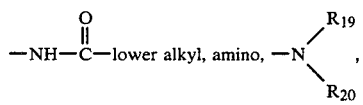
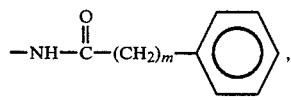
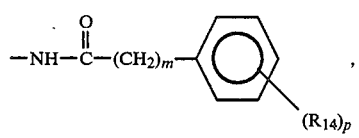
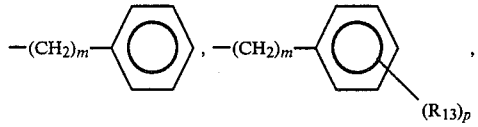
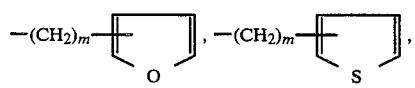
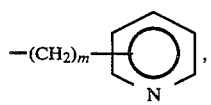
a 1- or 2-naphthyl of the formula
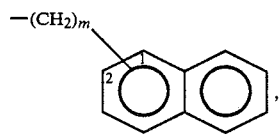
a substituted 1- or 2-naphthyl of the formula
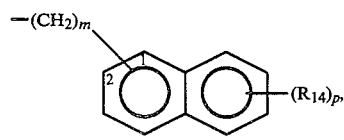
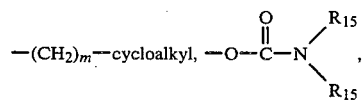
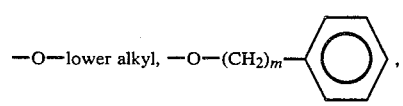
-continued
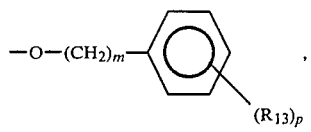
a 1- or 2-naphthyloxy of the formula
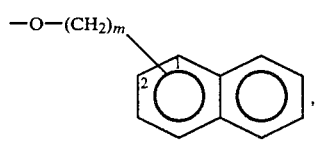
a substituted 1- or 2-naphthyloxy of the formula
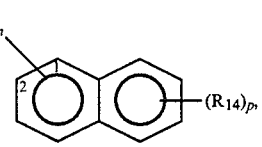
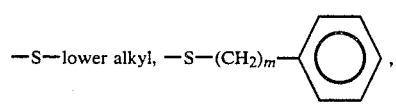
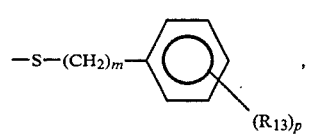
a 1- or 2-naphthylthio of the formula
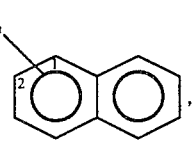
or a substituted 1- or 2-naphthylthio of the formula
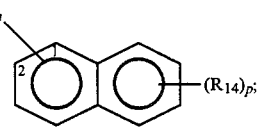
$R_8$ is halogen,
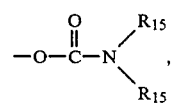
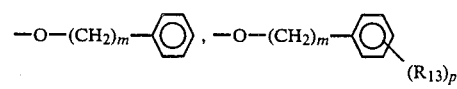
—O—lower alkyl, a 1- or 2-naphthyloxy of the formula

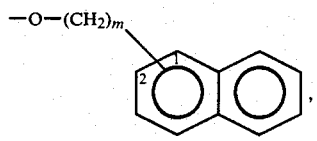

a substituted 1- or 2-naphthyloxy of the formula

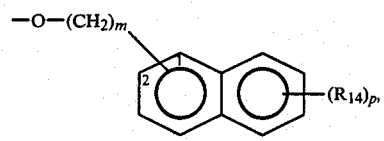

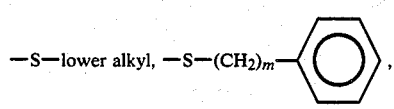

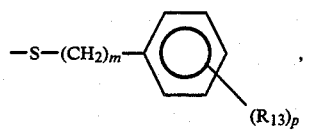

a 1- or 2-naphthylthio of the formula

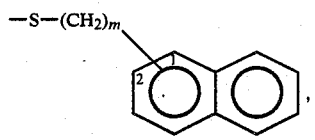

or a substituted 1- or 2-naphthylthio of the formula

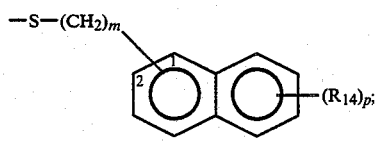

R$_9$ is keto,

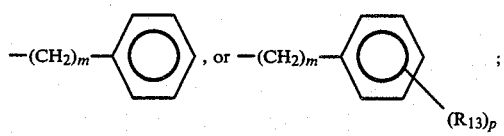

R$_{10}$ is halogen or —Y—R$_{16}$;
R$_{13}$ is lower alkyl of 1 to 4 carbons, lower alkoxy or 1 to 4 carbons, lower alkylthio of 1 to 4 carbons, chloro, bromo, fluoro, trifluoromethyl, hydroxy, phenyl, phenoxy, phenylthio, or phenylmethyl;
R$_{14}$ is lower alkyl of 1 to 4 carbons, lower alkoxy of 1 to 4 carbons, lower alkylthio of 1 to 4 carbons, chloro, bromo, fluoro, trifluoromethyl or hydroxy;
m is zero, one, two, three, or four;
p is one, two or three provided that p is more than one only if R$_{13}$ or R$_{14}$ is methyl, methoxy, chloro, or fluoro;
R$_{15}$ is hydrogen or lower alkyl of 1 to 4 carbons;
Y is oxygen or sulfur;
R$_{16}$ is lower alkyl of 1 to 4 carbons

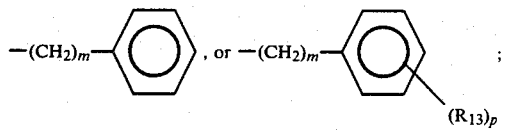

R$_{19}$ is lower alkyl, benzyl or phenethyl;
R$_{20}$ is hydrogen, lower alkyl, benzyl or phenethyl;
R$_1$ is hydrogen, lower alkyl, halo substituted lower alkyl,

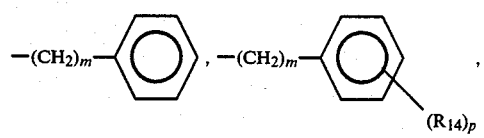

—(CH$_2$)$_m$—cycloalkyl, —(CH$_2$)$_2$—NH$_2$, —(CH$_2$)$_3$—NH$_2$,

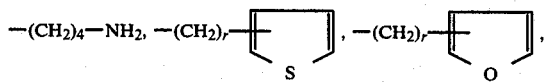

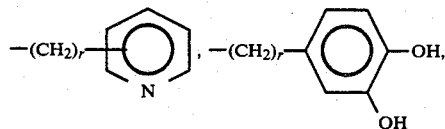

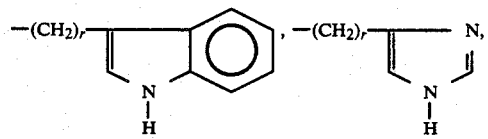

—(CH$_2$)$_r$—SH, or —(CH$_2$)$_r$—C(=O)—NH$_2$;

R$_2$ is lower alkyl, —(CH$_2$)$_m$—cycloalkyl,

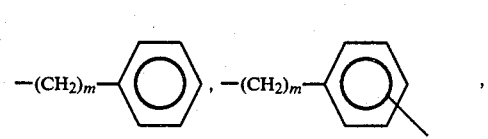

—(CH$_2$)$_v$—OH, —(CH$_2$)$_v$—NH$_2$, —(CH$_2$)$_v$—O—lower alkyl,
—(CH$_2$)$_v$—O—cycloalkyl, —(CH$_2$)$_v$—S—lower alkyl, —(CH$_2$)$_v$—S—cycloalkyl, —(CH$_2$)$_v$—NH—C(=O)—lower alkyl,

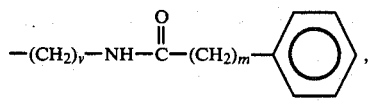

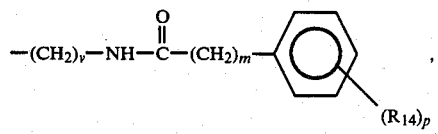

-continued

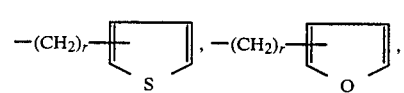

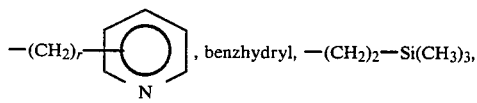

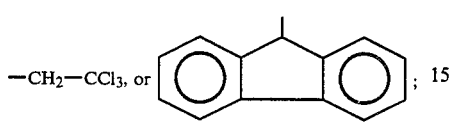

r is an integer from 1 to 4;
v is an integer from 2 to 4;
$R_3$ is hydrogen, lower alkyl,

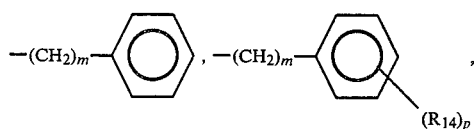

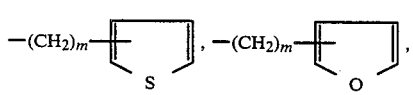

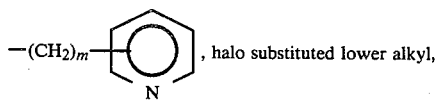

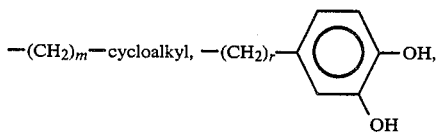

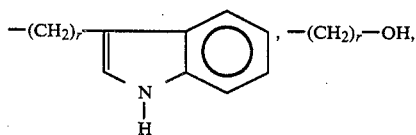

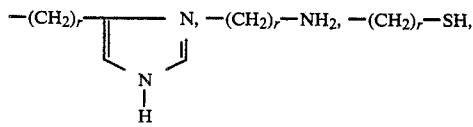

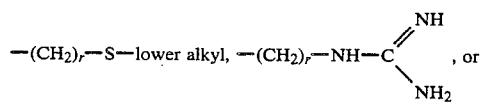

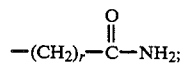

$R_6$ is hydrogen, lower alkyl, benzyl, benzhydryl,

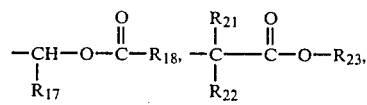

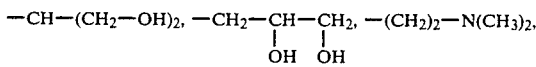

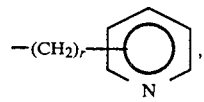

or a pharmaceutically acceptable salt forming ion;
$R_{17}$ is hydrogen, lower alkyl, cycloalkyl, or phenyl;
$R_{18}$ is hydrogen, lower alkyl, lower alkoxy or phenyl;
$R_{21}$ and $R_{22}$ are independently selected from hydrogen and lower alkyl; and
$R_{23}$ is lower alkyl.

2. A compound of claim 1 wherein:
X is

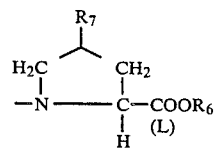

$R_6$ is hydrogen, phenyl methyl, or an alkyl metal salt ion;
$R_7$ is hydrogen, cyclohexyl, lower alkoxy of 1 to 4 carbons,

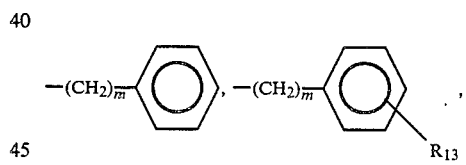

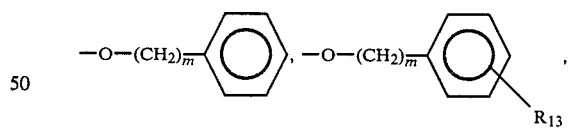

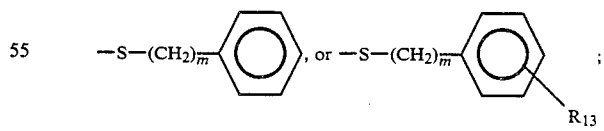

m is zero, one or two; and
$R_{13}$ is methyl, methoxy, methylthio, chloro, bromo, fluoro, or hydroxy.

3. A compound of claim 2 wherein
$R_1$ is straight or branched chain lower alkyl of 1 to 4 carbons;
$R_2$ is straight or branched chain lower alkyl of 1 to 4 carbons,

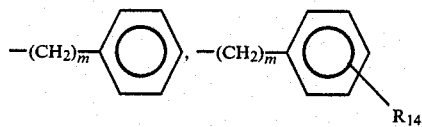

—(CH$_2$)$_m$—cycloalkyl wherein cycloalkyl is a saturated ring of 5 to 7 carbons, or —(CH$_2$)$_v$—O— lower alkyl wherein lower alkyl is straight or branched chain of 1 to 4 carbons;

R$_3$ is straight or branched chain lower alkyl of 1 to 4 carbons,

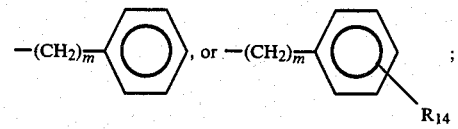

v is an integer from 2 to 4;
m is zero, one, or two; and
R$_{14}$ is methyl, methoxy, methylthio, Cl, Br, F, or hydroxy.

4. A compound of claim 3 wherein:
X is

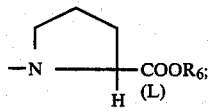

R$_1$ is methyl; and
R$_6$ is hydrogen or an alkali metal salt ion.

5. A compound of claim 4 wherein
R$_2$ is methyl, n-butyl, phenyl, cyclohexyl, or —(CH$_2$)$_2$—O—CH$_3$; and
R$_3$ is phenylmethyl.

6. The compound of claim 5, 1-[[[(S)-3-[(methoxycarbonyl)amino]-2-oxo-4-phenylbutyl]methylamino]carbonyl]-L-proline, monolithium salt.

7. The compound of claim 5, 1-[[[(S)-3-[(butoxycarbonyl)amino]-2-oxo-4-phenylbutyl]methylamino]carbonyl]-L-proline, monolithium salt.

8. The compound of claim 5, (S)-1-[[methyl-[2-oxo-3-[(phenoxycarbonyl)amino]-4-phenylbutyl]amino]carbonyl]-L-proline, monolithium salt.

9. The compound of claim 5, 1-[[[(S)-3-[(cyclohexylcarbonyl)amino]-2-oxo-4-phenylbutyl]methylamino]carbonyl]-L-proline, monolithium salt.

10. The compound of claim 5, 1-[[[(S)-3-[[(2-methoxyethoxy)carbonyl]amino]-2-oxo-4-phenylbutyl]methylamino]carbonyl]-L-proline, monolithium salt.

11. A compound of claim 3 wherein:
X is

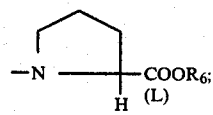

R$_6$ is phenylmethyl;
R$_1$ is methyl;
R$_2$ is —C(CH$_3$)$_3$; and
R$_3$ is phenylmethyl.

12. A pharmaceutical composition useful for treating hypertension comprising a pharmaceutically acceptable carrier and a hypotensively effective amount of a compound of the formula

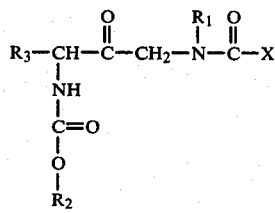

wherein R$_1$, R$_2$, R$_3$ and X are as defined in claim 1.

13. The method of treating hypertension in a mammalian host which comprises administering a hypotensively effective amount of the composition of claim 12.

* * * * *